United States Patent
Krivoruchko

(10) Patent No.: US 7,416,555 B2
(45) Date of Patent: Aug. 26, 2008

(54) INTRAVASCULAR MATERIAL REMOVAL DEVICE

(75) Inventor: Michael Krivoruchko, Forestville, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 472 days.

(21) Appl. No.: 11/085,738

(22) Filed: Mar. 21, 2005

(65) Prior Publication Data

US 2005/0165431 A1 Jul. 28, 2005

Related U.S. Application Data

(62) Division of application No. 10/423,266, filed on Apr. 25, 2003, now abandoned.

(51) Int. Cl.
*A61B 17/22* (2006.01)
(52) U.S. Cl. ........................................ 606/159
(58) Field of Classification Search ............ 606/159; 604/22, 267; 15/104.2, 104.16
See application file for complete search history.

(56) References Cited

U.S. PATENT DOCUMENTS

| | | | |
|---|---|---|---|
| 4,857,046 A | 8/1989 | Stevens et al. | |
| 5,030,201 A | 7/1991 | Palestrant | |
| 5,087,265 A | 2/1992 | Summers | |
| 5,176,693 A | 1/1993 | Pannek, Jr. | |
| 5,195,954 A | 3/1993 | Schnepp-Resch et al. | |
| 5,632,755 A | 5/1997 | Nordgren et al. | |
| 5,746,758 A | 5/1998 | Nordgren et al. | |
| 5,882,332 A | 3/1999 | Wijay | |
| 5,895,400 A * | 4/1999 | Abela ................ 606/159 |
| 5,947,985 A | 9/1999 | Imran | |
| 6,030,397 A | 2/2000 | Monetti et al. | |
| 6,302,870 B1 * | 10/2001 | Jacobsen et al. ........ 604/272 |

* cited by examiner

*Primary Examiner*—Corrine McDermott
*Assistant Examiner*—Christopher D Prone

(57) ABSTRACT

An intravascular material removal device that removes material from a vessel wall and creates flow dynamics that draw the material into a catheter device for removal from the vessel is provided. A collapsible device that provides a relatively low delivery profile while being expandable in use to adapt to varying and variable vessel diameters is also provided. A spiral configured material removing element is provided that can adapt to varying vessel diameters and to remove material forming blockages or occlusions from the inner wall of a vessel.

16 Claims, 7 Drawing Sheets

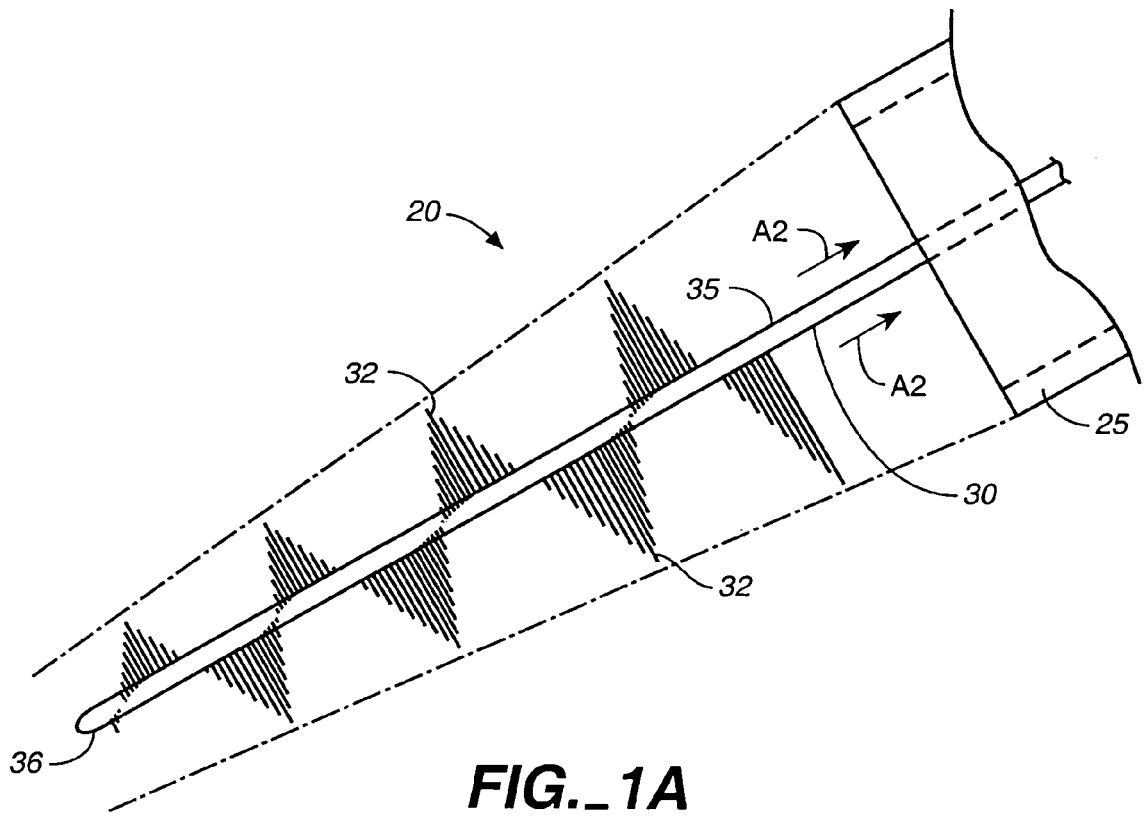
FIG._1A
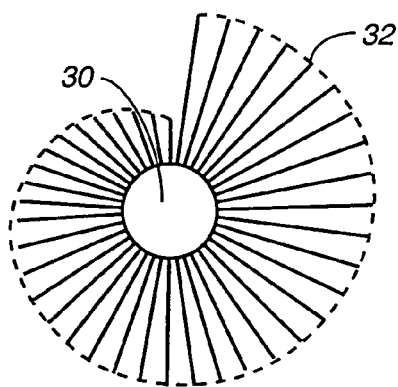
FIG._1B

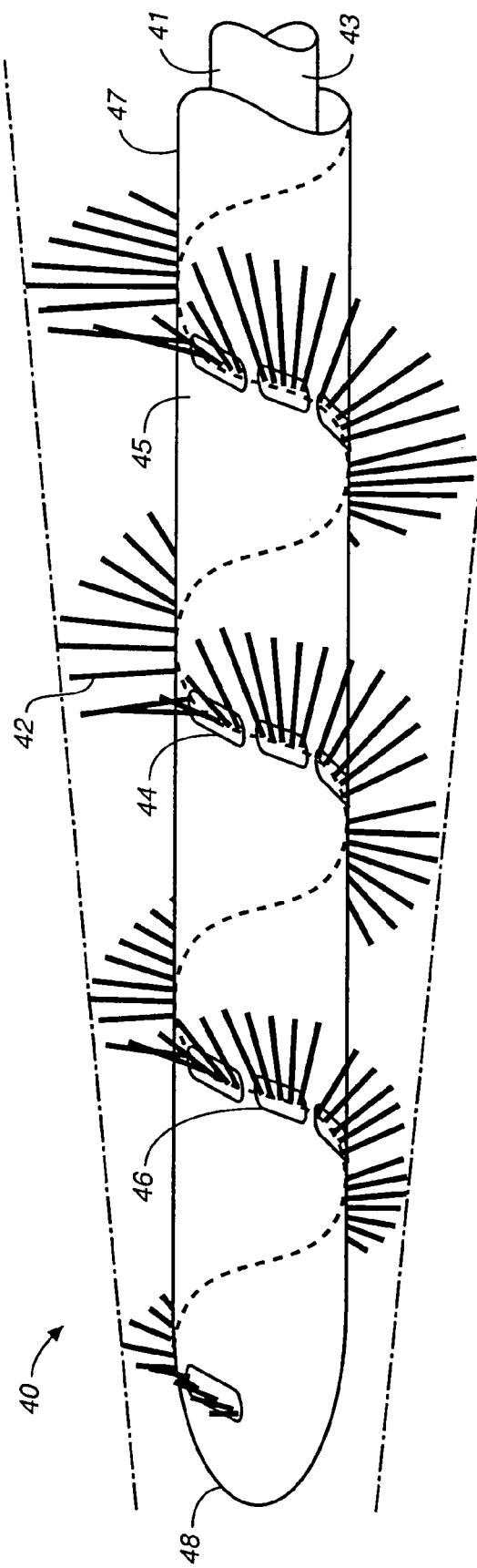
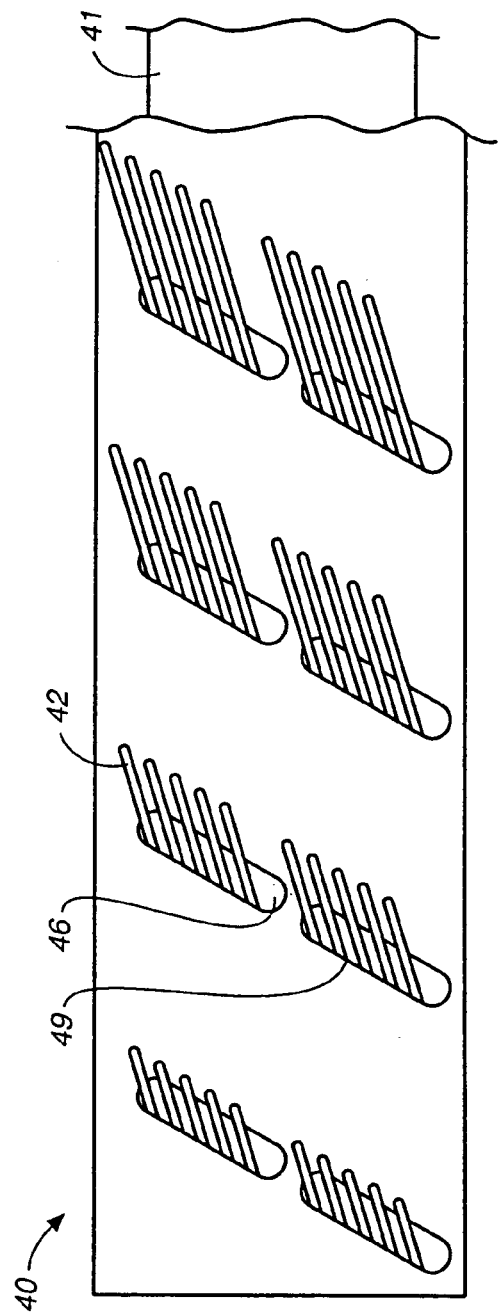
FIG._2A
FIG._2D

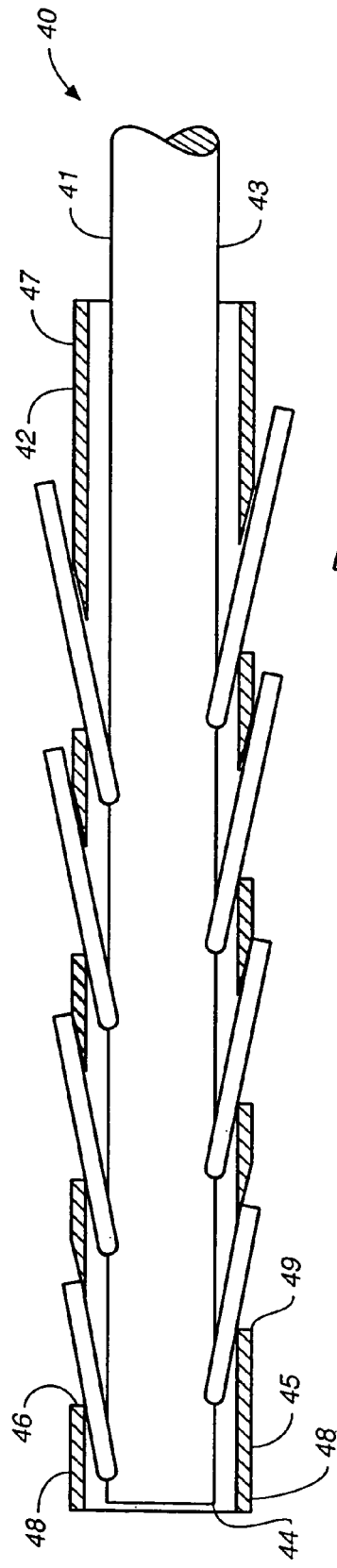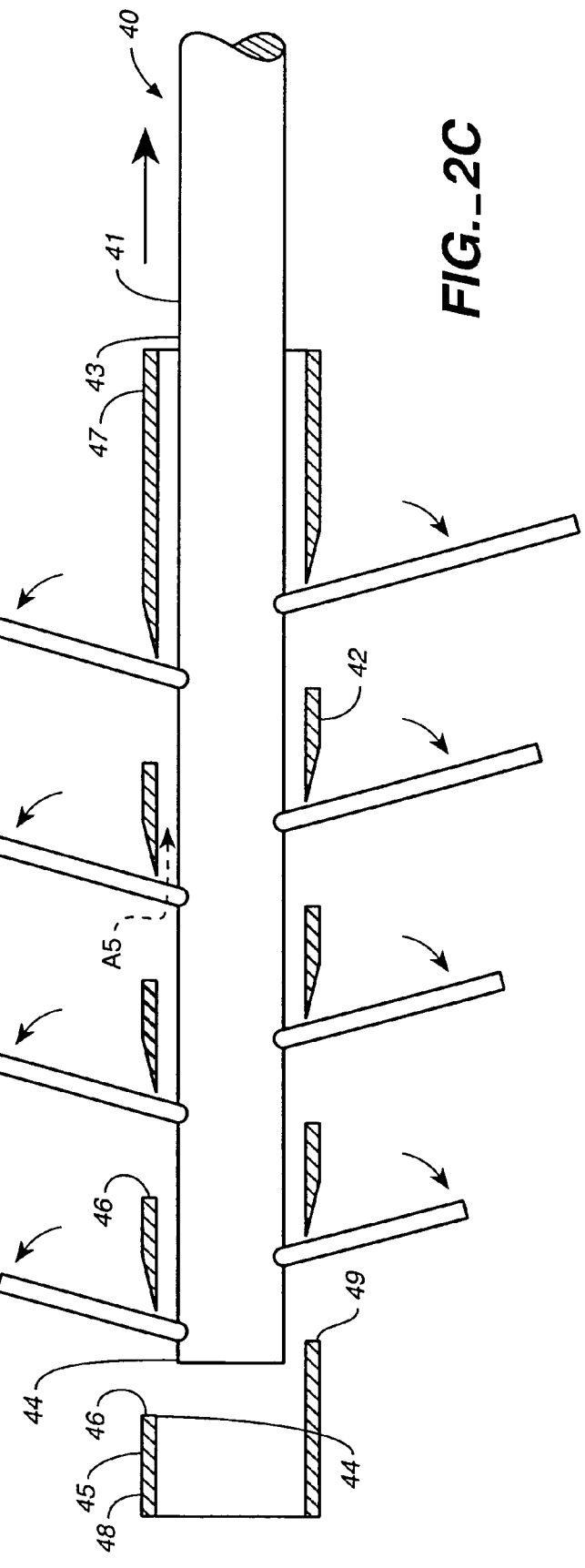

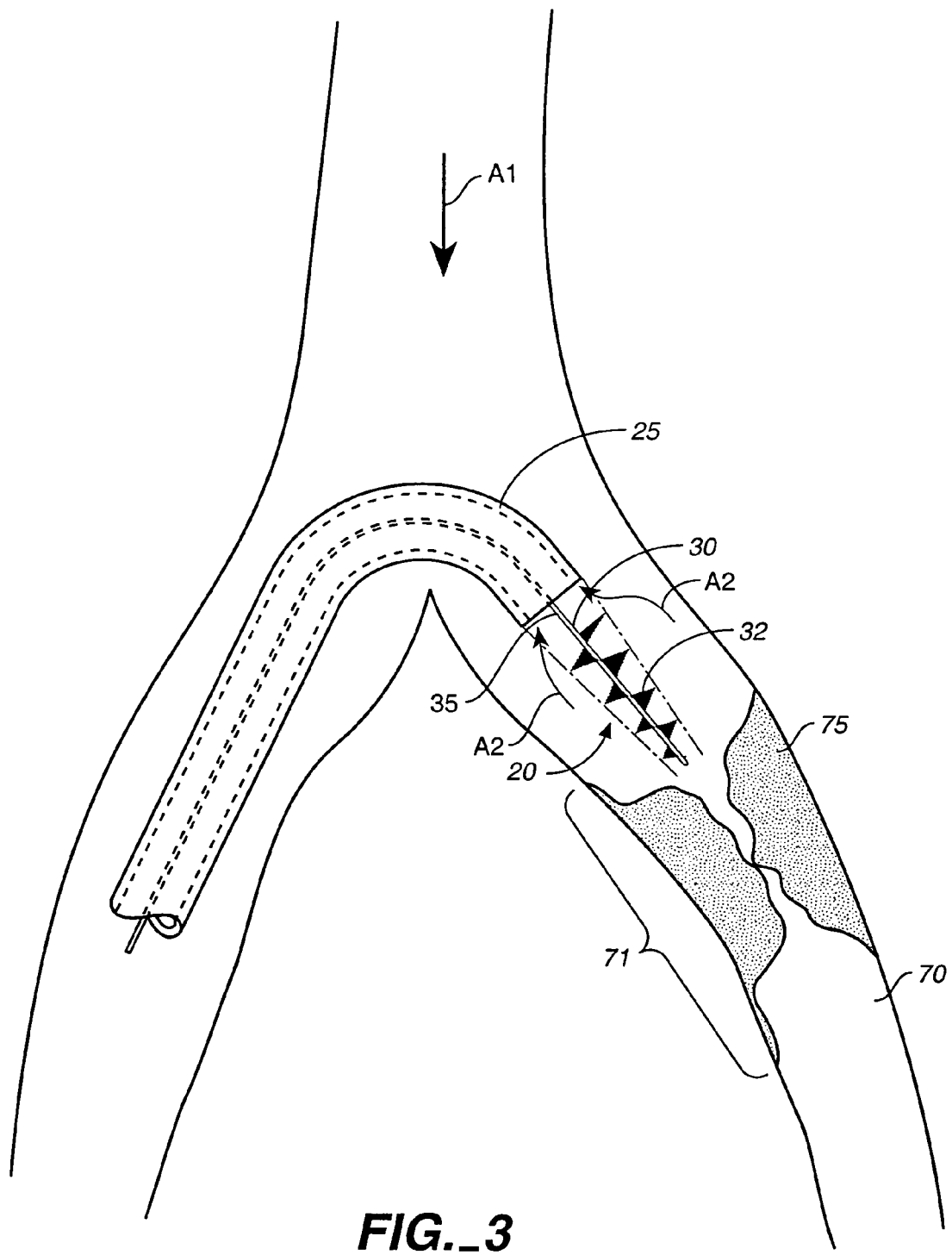
FIG._3

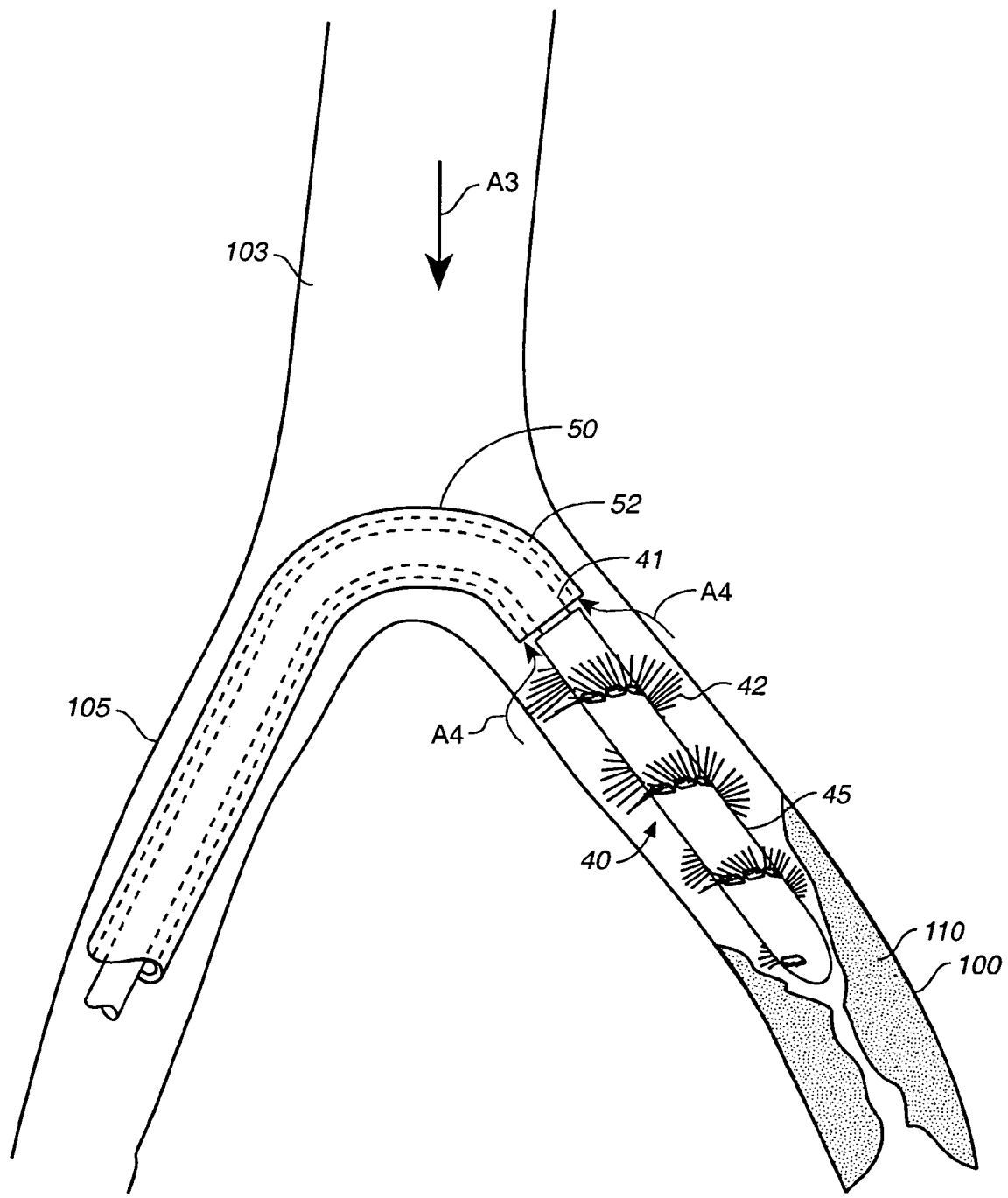
FIG._4

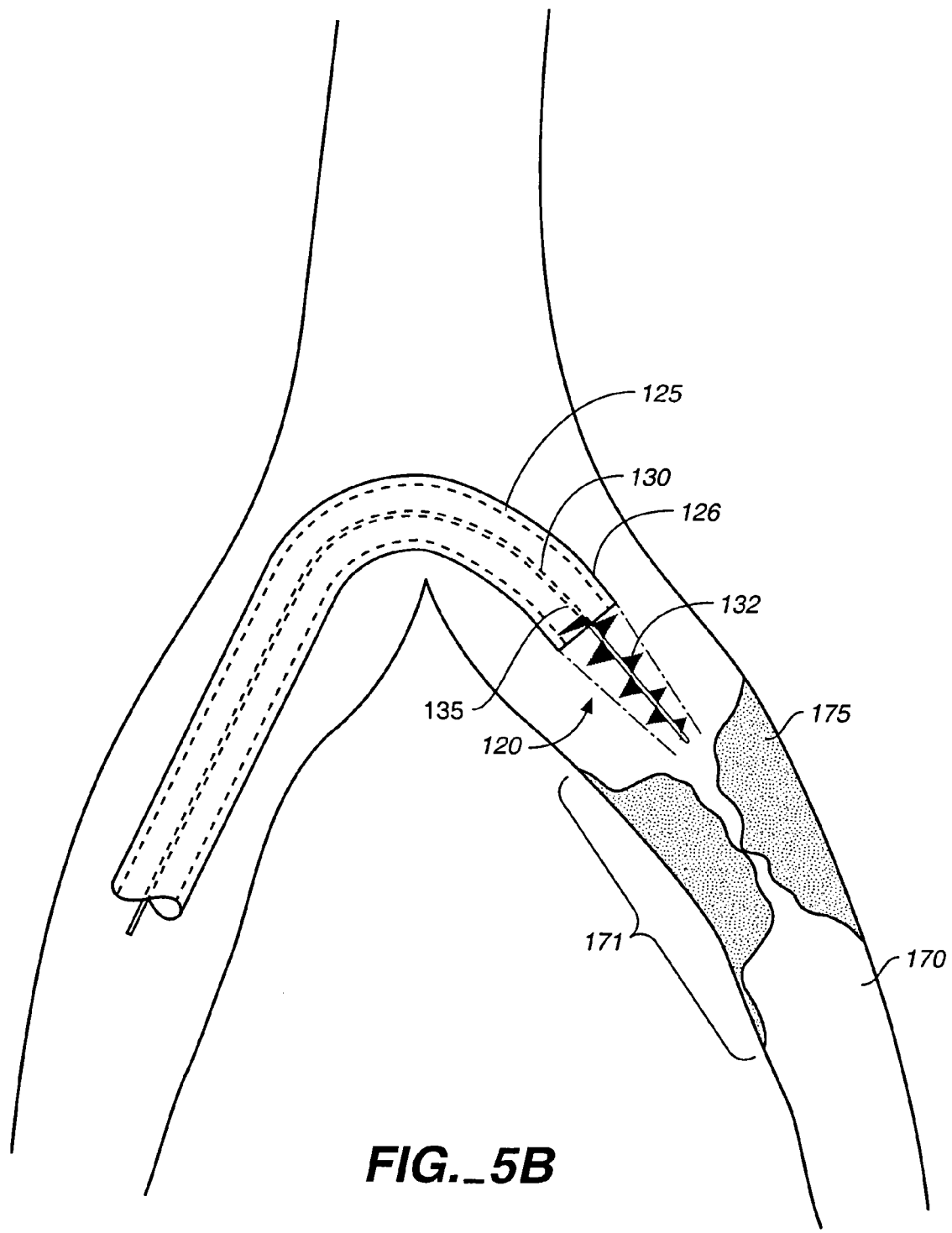
FIG._5B

INTRAVASCULAR MATERIAL REMOVAL DEVICE

RELATED APPLICATIONS

This application is a divisional of U.S. application Ser. No. 10/423,266 filed Apr. 25, 2003, the entire contents of which are hereby incorporated by reference.

FIELD OF THE INVENTION

The invention relates to a device for removing material such as thrombus, plaque, and clots, from a body lumen such as a blood vessel.

BACKGROUND OF THE INVENTION

Plaque, fat deposits, calcium deposits, thrombus, blood clots, etc. deposited on the inner walls of the blood vessel may cause narrowing or occlusion of the blood vessels, cutting off or restricting blood flow and/or presenting a dangerous condition in which the material may break off and travel through the vasculature causing further blockages, clots or embolisms.

A variety of devices have been proposed for forming a channel in or removing such material from a vessel.

Guidewires have been used to channel through such deposits and a balloon passed over the guidewire is then used to form an opening. This method, however, does not provide a means for removing the material deposited on the vessel wall. Also material can break off and move downstream forming a clot or other blockage.

Another technique has used laser ablation to form channels in the blockages. The laser energy atomizes or blasts away particles of occluding materials. Laser techniques currently used carry with them the risk of overheating tissue and burning holes in the vessel walls. The openings formed in the blockages are also limited by the size of the laser. The laser treatment is typically followed with ballooning of the occluded region.

Some techniques have used percutaneously placed catheter devices to physically remove material. The percutaneous techniques avoid direct surgery at the occluded site and avoid creation of a large opening at the site of insertion into the blood vessel. Rotating cylindrical cutters have been used to shave off material from the vessel wall. These devices have been problematic where the cut material moves downstream forming another blockage or clot. Such devices also have not worked particularly well on thrombus or clots. Also, the large cutting head size relative to the delivery path, that is required to effectively remove material from the vessel wall, makes the cutting device difficult to deliver. A variety of cutting head configurations have been proposed including a conical cutting head with aspiration for retrieving cut material. A screw like conical cutting head has also been proposed.

A balloon expandable cutting device has been proposed so the diameter of the cutting head may be varied to accommodate blood vessels having a wide range of internal diameters. However, these devices require actuation to expand or contract the cutting heads and they do not adapt sufficiently to change in circumference of the vessel along its length or as the device is advanced through the vessel while cutting.

Another device uses highly pressurized fluid to remove material. This technique includes a risk of perforation and damage to vessel from the high pressure jetted fluid. It is also a slow process that takes significant physician and patient table time to perform.

Other devices have used inflated balloons on each side of the occluded portion of the vessel to be treated, to stop flow of blood while a mechanism such as a rotating cutter, stream of fluid or rotating brush is used to dislodge particles. These devices are relatively complex requiring placement of a balloon on each side of the blockage.

Accordingly it would be desirable to provide a device for removing material from a body lumen that has a relatively small delivery profile and a relatively simple delivery procedure. It would also be desirable to provide a device for removing material from a body lumen that is adaptable to varying sizes of blood vessels diameters. It would also be desirable to provide such an improved device that reduces the risk of dislodged or cut materials moving downstream and forming blockages or clots.

SUMMARY OF THE INVENTION

An embodiment according to the present invention provides an intravascular material removal device that removes material from a vessel wall and creates flow dynamics that draw the material into a catheter device for removal from the vessel. A collapsible device provides a relatively low delivery profile while being expandable in use to adapt to varying and variable vessel diameters.

In one embodiment according to the present invention, the device comprises a plurality of bristles formed in a spiral-like configuration along the length of an elongate member. In use the elongate member is rotated so that the spiraled bristles create a flow pattern in a proximal direction that draws materials dislodged by the bristles or brush towards a catheter from which the elongate member extends.

The device has a material removing element that may be selected from a plurality of material removing elements having different properties, e.g., stiffness, flexibility, bristles of various sizes, etc for removing different types of material from gelatinous deposits like thrombus to harder deposits such as calcium deposits.

Another aspect according to the invention may provide a material removal device having bristles constructed of a material that permits the bristles to flex to conform to the vasculature as it is moved through or is deployed in a vessel, and that is sufficiently stiff to remove desired material from the vessel wall.

Another aspect according to the invention, provides a spiral configuration where the length of the bristles at a distal end portion are shorter that the length of the bristles at a proximal end portion such that the overall diameter of the device is greater at the proximal end portion than at the distal end portion.

In one variation of the embodiment, the bristles are retractable so that the delivery profile of the device may be reduced for delivery through the vasculature. The device in one variation provides bristles that may flex when retracted into a catheter. Another embodiment provides an inner elongate member with a plurality of bristles formed in a spiral-like configuration attached to the inner member and an outer member positioned over the elongate member having at least one opening through which the bristles may extend. The outer member and inner member are configured to move axially with respect to each other so that the outer member engages to retract the bristles to provide a smaller radius device or alternatively permit the bristles to extend through the opening to a produce a larger radius device.

Aspiration may be provided through a catheter into which material is drawn and/or through the material removing element itself which may have openings through slots in an outer member and through a series of bristles.

BRIEF DESCRIPTION OF THE DRAWINGS

FIG. 1A is a side view of an embodiment of a device for removing material deposited on vessel walls.

FIG. 1B is a view from the proximal end of the device of FIG. 1B

FIG. 2A is a side view of an embodiment of a device for removing material deposited on vessel walls.

FIG. 2B is a side view, partial cross section of a portion of the device of FIG. 2A in a partially collapsed position.

FIG. 2C is a side view, partial cross section of a portion of the device of FIG. 2A in an expanded position.

FIG. 2D is a schematic side view of a portion of the device of FIG. 2A.

FIG. 3 illustrates the device of FIG. 1A in use, percutaneously positioned in a partially blocked iliac artery of a patient.

FIG. 4 illustrates the device of FIGS. 2A-2D in use, percutaneously positioned in a blocked iliac artery of a patient.

FIG. 5B illustrates the device of FIG. 5A in use, percutaneously positioned in a partially blocked iliac artery of a patient.

DETAILED DESCRIPTION

Figure 5A:
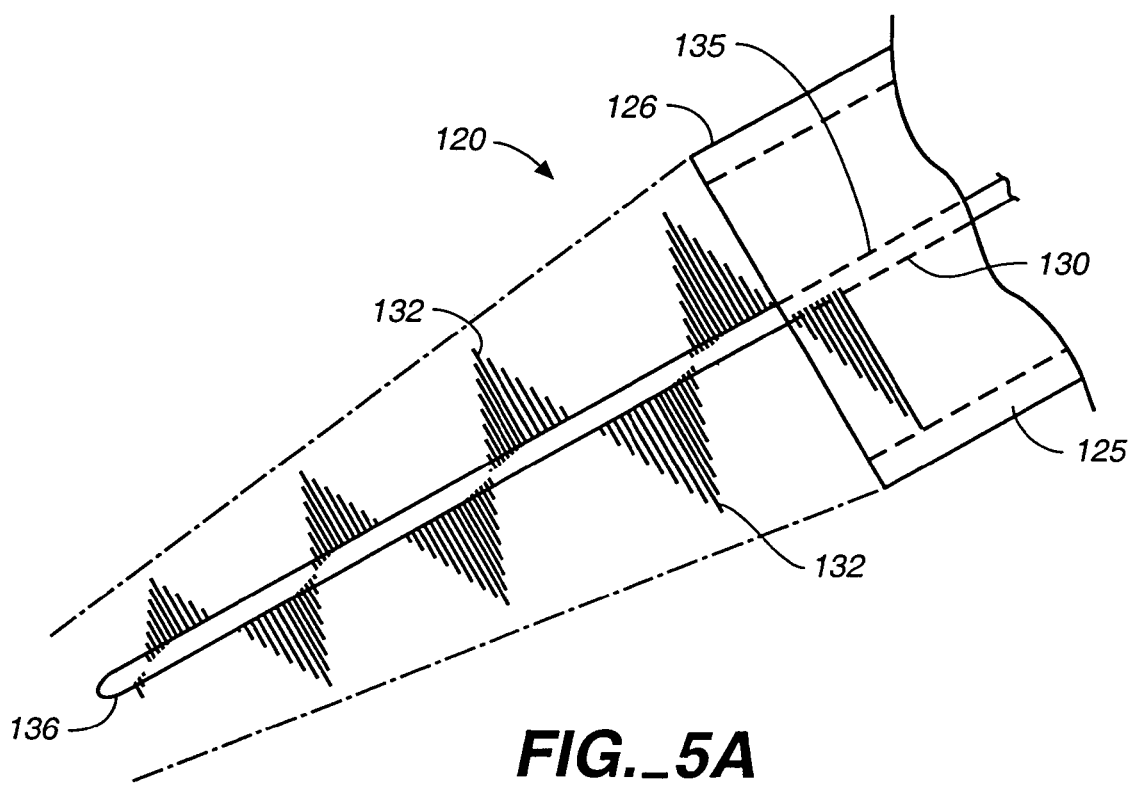
FIG. 5A is a side view of an embodiment of a device for removing material deposited on vessel walls.

Referring to FIGS. 1A and 1B, an intravascular material removing device 20 is illustrated including a delivery catheter 25 and an elongate member 30 with a plurality of bristles 32 formed in a spiral arrangement along the length of the elongate member 30. The elongate member 30 is illustrated in a position extending out of a delivery catheter 25. The limits of the arc circumscribed by the bristles 32 gradually taper from a proximal portion 35 to a distal end portion 36 of the elongate member 30. When the elongate member 30 is retracted into the delivery catheter 25, the bristles 32 may flex or bend so that they fit within the delivery catheter 25. Thus the elongate member 30 is retractable into a catheter having a smaller diameter than the outer diameter of the elongate member when the bristles are not constrained.

As illustrated in FIG. 3, in use, the elongate member is delivered percutaneously through the catheter 25 to a blocked portion 71 of a vessel 70. In this particular embodiment, an abdominal aorta is illustrated with one of the iliac vessels partially blocked by material 75. Expanded within a vessel, the bristles 32 adapt to a varying diameter vessel and are in position to remove material. The elongate member 30 is placed adjacent the material 75 and is rotated by a motor (not shown) coupled to the elongate member 30 located external the patient's body. As the elongate member 30 is rotated, it is advanced into and through the blocked material 75, the narrower distal end 36 first and then the wider proximal end portion 35, the bristles 32 being flexible, adapting to the diameter of the vessel as the elongate member 30 is moved within the vessel. The bristles 32 break the material 75 away from the vessel wall and create a pressure gradient or flow in a direction towards the catheter 25 and proximal end portion 35, like a screw pump. The arrow A1 illustrates the normal direction of the flow of blood while the arrows A2 illustrate the direction of flow of material when the device 20 is in use. The catheter 25 may also provide aspiration to further draw the material into the catheter 25.

The bristles 32 may be made of a number of different materials such as nylon or a metal. The stiffness/flexibility, hardness/softness, abrasiveness, thickness of, number of and configuration of the bristles 32 may be selected depending upon the application, e.g., the material to be removed or the condition of the vessel in which it is to be used. For example, stiffer bristles would be used for fibrotic material or calcium deposits whereas for blood, thrombosis and gelatinous material, a softer bristle may be selected. A plurality of material removing elements may be provided, each having a different property that may be selected based upon condition of the vessel to be treated, i.e., the type of material deposited on the vessel wall, the type of vessel, or the toughness, resilience or other property of the vessel or vessel wall.

Referring to FIGS. 2A-2D an intravascular material removal device 40 is illustrated. The device 40 comprises an inner member 41 having bristles 42 coupled to the inner member 41, and a cylindrical outer member 45 having a distal portion 48 including slots 46 formed in the outer member 45 in a generally spiral configuration along the length of the distal portion 48. The bristles 42 of the inner member 41 are affixed at an angle or alternatively are hinged or otherwise coupled to the inner member 41, also in a spiral configuration. The limits of the arc circumscribed by the bristles 42 gradually taper from a proximal portion 43 to a distal end portion 44 of the inner member 41. The bristles 42 extend through the slots 46 in the outer member 45. The bristles 42 are formed of a biocompatible material such as, e.g. a nylon material. The biocompatible material may be selected based on factors such as stiffness depending on its desired application, the type or characteristics of material that is to be removed or the type or characteristic of the vessel in which it is to be used such as e.g. described above with reference to device 20.

The inner member 41 slides coaxially within the outer member 45 to expand or collapse, or extend or retract the bristles 42 extending out of the slots 46. As illustrated in FIG. 2B, the device is in a retracted position in which the radius of the device 40 is reduced. In this position the distal end 44 of the inner member 41 extends distally toward the distal end 48 of the outer member 45. The bristles 42 are drawn into the slots 46 by edges 49 of the slots 46.

As illustrated in FIGS. 2A and 2C, the device 40 is in a fully expanded position with the bristles 42 extending out of the slots 46. In this position, the distal end 44 of the inner member 41 is moved in a proximal direction with respect to the distal end 48 of the outer member 45 so that the bristles 42 are not constrained by the edges 49 of the slots 46 and extend to their full radius. Expanded within a vessel, the bristles 42 adapt to a varying diameter vessel and are in position to remove material. The bristles 42 are ideally flexible enough to avoid damage when expanding to the vessel diameter, while being stiff enough to removed the deposited material.

FIG. 4A illustrates a device 40 in use in removing a blockage 110 from an iliac artery branch vessel 100. The device is percutaneously passed in a retracted position within a catheter 50, into the right iliac artery 105 upstream through the abdominal aorta 103 and back down into the left iliac branch vessel 100. The device 40 is initially positioned out of the catheter 50 and in the artery 105, in a retracted position as illustrated in FIG. 2B, and upstream and adjacent the blockage 110. Once the device 40 is in position, the inner member 41 is moved proximally with respect to the outer member 45 to expand the device 40 so that the bristles 42 engage the inner wall of the vessel 100. The inner member 41 may be moved to partially or completely release the bristles 42 from engagement with the edges 49 of the slots 46 depending on the desired device radius. The bristles 42 further adapt to the diameter of the vessel. The device 40 is then rotated about its axis a so that the bristles 42 scrape off the material and create a flow like a screw pump in an upstream direction towards the distal end 52 of the catheter 50. According to one variation of this embodiment the inner member 41 and outer member 45 have some clearance between each other so that irrigation and aspiration may be provided through the slots 46 as shown for example by arrow A5 in FIG. 2C. Alternatively or in addition, irrigation and aspiration may be provided through the distal end of the catheter 50. Thus, a screw pump like creation of a flow pattern moves material upstream and thereby avoids loosened or cut materials from moving downstream. The bristles 42 may be sufficiently flexible that the device 40 may retracted into the catheter 50 in its fully or partially expanded position during delivery or removal of the device 40.

Referring to FIGS. 5A and 5B, an intravascular material removing device 120 is illustrated including a delivery catheter 125 and an elongate member 130 with a plurality of bristles 132 formed in a spiral arrangement along the length of the elongate member 130. The device 120 is constructed in a manner similar to the device 20 described above with reference to FIGS. 1A-B and FIG. 3. The elongate member 130 is illustrated in a position extending out of a delivery catheter 125 with the proximal portion 135 of the elongate member 130 positioned within the distal portion 126 of the catheter 125. The limits of the arc circumscribed by the bristles 132 gradually taper from a proximal portion 135 to a distal end portion 136 of the elongate member 130, and such that when the elongate member 130 is retracted into the delivery catheter 125, the bristles 132 fit within the delivery catheter 125.

As illustrated in FIG. 3, in use, the elongate member 130 is delivered percutaneously through the catheter 125 to a blocked portion 171 of a vessel 170. In this particular embodiment, an abdominal aorta is illustrated with one of the iliac vessels partially blocked by material 175. The elongate member 130 is placed adjacent the material 175 and is rotated by a motor (not shown) coupled to the elongate member 130 located external the patient's body. The bristles 132 break the material 175 away from the vessel wall and create a pressure gradient or flow into the catheter 125 wherein the distal portion 126 of the catheter 125 envelopes the proximal portion 135 of the elongate member 130 and bristles 132, thereby providing an impeller to further direct material into the catheter 125.

The devices of embodiments of the invention are illustrated in use in a blocked iliac artery. Other blocked vessels are contemplated for treatment with the device, including for example, without limitation, the carotid artery, superficial femoral artery and popliteal artery.

While the invention has been described with reference to particular embodiments, it will be understood to one skilled in the art that variations and modifications may be made in form and detail without departing from the spirit and scope of the invention.

What is claimed is:

1. An intravascular material removal device, comprising:
   a first elongate member having a plurality of bristles extending outwardly therefrom, said bristles being disposed at various positions along a length of the first elongate member,
   a second elongate member having bristle receiving openings disposed at various longitudinal positions along a length of the second elongate member, wherein each of the openings receive a plurality of the bristles,
   said first elongate member being movable relative to said second elongate member, wherein relative movement between said first elongate member and said second elongate member alters a length of outward extension of said bristles from said first elongate member.

2. An intravascular material removal device according to claim 1, wherein said bristles are arranged in a generally spiral configuration, and wherein the first elongate member is rotatable about its length so that the spiral bristles produce a partially axial flow pattern.

3. The intravascular material removal device of claim 2, wherein the spiral bristles have a variable length along the first elongate member.

4. The intravascular material removal device of claim 2, wherein the spiral bristles are configured to adapt to a diameter of a vessel in which it is located.

5. The intravascular material removal device of claim 2, wherein the spiral bristles taper from a proximal portion of the first elongate member to a distal portion of the first elongate member.

6. The intravascular material removal device of claim 1, wherein said openings are provided in a generally spiral pattern along a length of the second elongate member.

7. The intravascular material removal device of claim 6, wherein said bristles extend through said openings so as to be in a generally spiral configuration.

8. The intravascular material removal device of claim 7, wherein the bristles are arranged in a generally spiral configuration on said first elongate member.

9. The intravascular material removal device of claim 6, wherein the first and second elongate members are retractable into a catheter.

10. The intravascular material removal device of claim 1, further comprising a catheter, wherein the catheter has an inner diameter and the bristles have a maximum radial extension that defines an outer diameter of said first elongate member, wherein the catheter inner diameter is smaller than the outer diameter of the first elongate member as defined by said maximum radial extension of said bristles.

11. An intravascular material removal device of claim 1, wherein said relative movement alters regions of contact on said bristles with respect to edges defining said openings in said second elongate member so as to alter the amount of radial extension of the bristles.

12. An intravascular material removal device comprising:
   an elongate member comprising:
      an inner spiral-like element including a plurality of bristles extending radially from the inner spiral-like element, wherein the elongate member is rotatable about its length so that the inner spiral-like element produces a partially axial flow pattern; and
      an outer member positioned over at least a portion of the inner spiral-like element, the outer member having a plurality of openings, each opening receiving a plurality of the bristles, wherein the outer member is axially moveable with respect to the inner spiral-like element so that the outer member engages the inner spiral-like element to move the inner spiral-like element from a first position to a second position, wherein in the first position the inner spiral-like element has a first diameter and in the second position the inner spiral-like element has a second diameter smaller than the first diameter.

13. An intravascular material removal device comprising:
   means for dislodging material from a vessel wall, wherein the dislodging means comprises means for producing a partially axial flow pattern, and means for adjusting a diameter of the dislodging means along varying longitudinal positions of said dislodging means, wherein the dislodging means includes at least one opening and a plurality of bristles extending outwardly from said means for producing the partially axial flow pattern through the at least one opening.

14. The intravascular material removal device of claim 13, wherein the means for producing the partially axial flow pattern comprises a spiral brush.

15. The intravascular material removal device of claim 13, further comprising a catheter into which the adjusting means and the means for producing the partially axial flow pattern are received.

16. An intravascular material removal device, comprising:

an inner elongate member, and bristles extending radially from the inner elongate member, said bristles longitudinally disposed along a length of the inner elongate member;

an outer elongate member having a longitudinal passage through which the inner elongate member extends, said outer elongate member having radial openings disposed along a length thereof, said radial openings each arranged to permit a plurality of the bristles to pass therethrough, said openings being defined by edges;

wherein relative movement between said inner elongate member and said outer elongate member adjusts a relative position therebetween, so as to adjust points of contact between said bristles and edges, and thereby control a length of radial extension of said bristles through said openings.

* * * * *